United States Patent
Rodriguez Oquendo

(10) Patent No.: US 9,334,538 B2
(45) Date of Patent: May 10, 2016

(54) METHOD FOR PRE-SCREENING AND CORRELATION OF UNDERLYING SCARB1 GENE VARIATION TO INFERTILITY IN WOMEN AND THERAPEUTIC USE OF PROGESTATIONAL AND OTHER MEDICATIONS IN TREATMENT

(71) Applicant: Annabelle Rodriguez Oquendo, Farmington, CT (US)

(72) Inventor: Annabelle Rodriguez Oquendo, Farmington, CT (US)

(*) Notice: Subject to any disclaimer, the term of this patent is extended or adjusted under 35 U.S.C. 154(b) by 284 days.

(21) Appl. No.: 13/707,256

(22) Filed: Dec. 6, 2012

(65) Prior Publication Data

US 2013/0345187 A1    Dec. 26, 2013

Related U.S. Application Data

(60) Provisional application No. 61/567,319, filed on Dec. 6, 2011.

(51) Int. Cl.

| | |
|---|---|
| *C12Q 1/68* | (2006.01) |
| *C12P 19/34* | (2006.01) |
| *A61K 31/10* | (2006.01) |
| *A61K 31/57* | (2006.01) |
| *A61K 45/06* | (2006.01) |
| *A61K 31/095* | (2006.01) |

(52) U.S. Cl.
CPC ............ *C12Q 1/6883* (2013.01); *A61K 31/095* (2013.01); *A61K 31/10* (2013.01); *A61K 31/57* (2013.01); *A61K 45/06* (2013.01); *C12Q 2600/156* (2013.01)

(58) Field of Classification Search
None
See application file for complete search history.

(56) References Cited

U.S. PATENT DOCUMENTS 7,208,467 B2    4/2007   Krieger et al.

OTHER PUBLICATIONS

Juppner; Bone, vol. 17; 1995, pp. 39S-40S.*
Lucentini (The Scientist; 2004, vol. 24, p. 20).*
Hegele (Arterioscler. Thromb. Vasc. Biol.; 2002, vol. 22, pp. 1058-1061).*
Yates et al; Human Reproduction, vol. 26, pp. 1910-1916, 2011.*
Melissa Yates, Antonina Kolmakova, Yulian Zhao and Annabelle Rodriguez; 'Clinical Impact of Scavenger Receptor Class B Type I Gene Polymorphisms on Human Female Fertility', Hum. Reprod. (2011).

* cited by examiner

*Primary Examiner* — Jehanne Sitton
(74) *Attorney, Agent, or Firm* — Ober, Kaler, Grimes & Shriver; Royal W. Craig

(57) ABSTRACT

A method of genotyping women experiencing infertility for non-physical reasons in order to identify the presence of the rs4238001 and/or rs10846744 mutation of the SCARB1 gene and, upon identifying the presence of one or both genetic mutations, administering a tailored therapeutic regimen to restore fertility by either one or a combination of 1) mediating the flux of cholesterol resulting from the mutation by therapeutic use of the cholesterol medication probucol and/or other cholesterol altering medications, and/or 2) amplifying the presence of hormone progesterone by therapeutic use of progestational and progestin medications.

10 Claims, 4 Drawing Sheets

METHOD FOR PRE-SCREENING AND CORRELATION OF UNDERLYING SCARB1 GENE VARIATION TO INFERTILITY IN WOMEN AND THERAPEUTIC USE OF PROGESTATIONAL AND OTHER MEDICATIONS IN TREATMENT

CROSS-REFERENCE TO RELATED APPLICATION

This application claims the benefit under 35 U.S.C. §119(e) of U.S. Provisional Application Ser. No. 61/567,319, filed Dec. 6, 2011, which is incorporated herein by reference.

BACKGROUND OF THE INVENTION

1. Field of the Invention

The present invention relates to genetic testing for a variation of the scavenger receptor class B type 1 gene (SCARB1) to ascertain a potential cause of infertility in women combined with the therapeutic use of progestational and other medications in the treatment of said infertility.

2. Description of the Background

Infertility in women is a major and increasing problem as the average age of the mother at conception has increased in recent decades. Infertility has many causes ranging from physical issues such as a blockage of the Fallopian tubes to hormonal imbalances. In some cases the cause of a woman's infertility is never satisfactorily determined. In such cases, women may be treated in an ad hoc manner by which different therapies are tried ad seriatim to see if fertility can be improved and pregnancy achieved. Therapies may include lifestyle and dietary changes, drug therapies and hormone modification therapies. For Example, U.S. Pat. No. 7,208,467 to Krieger et al. issued Apr. 24, 2007 suggests the use of therapeutic lipid-altering compositions for the treatment of infertility.

Progesterone is a female steroid hormone secreted by corpus luteum during the process of ovulation which is vital for a successful conception and healthy pregnancy. Progesterone plays a major role in regulating the menstrual cycle and preparing the uterus for conception and pregnancy The major function of progesterone is to prepare the endometrium for implantation of the fertilized egg by promoting tissue development and blood supply. Increases in progesterone levels strengthen and maintain the endometrium in order to allow it to support the embryo throughout pregnancy and also prevents premature shedding (i.e., menstruation). Low progesterone is a known cause of infertility in women.

Recently evidence suggests that a variation of the scavenger receptor class B type 1 gene (SCARB1) involved in regulating cholesterol in the bloodstream also affects progesterone production in women, making it a likely cause in a substantial number of hormone imbalance infertility cases. See, Melissa Yates, Antonina Kolmakova, Yulian Zhao and Annabelle Rodriguez, "Clinical Impact Of Scavenger Receptor Class B Type I Gene Polymorphisms On Human Female Fertility" (Hum. Reprod. July; vol. 2, No. 7: pp. 1910-16 (advanced access publication Apr. 30, 2011) which is incorporated herein by reference. Scavenger receptor class B type 1 (SR-BI) is a physiologically relevant lipoprotein receptor that functions by mediating the selective uptake of neutral lipids in highly expressive tissues such as the liver, adrenals, and ovaries. It is thought to exert a major role in reverse cholesterol transport, a process by which plasma cholesterol is delivered to the liver for bile acid production. In addition, SR-BI has been shown to mediate cholesterol uptake in steroidogenic tissue for hormone production. In humans, the SR-BI gene (SCARB1) (formerly referred to as CLA-1) is localized to chromosome 12 (12q24.31) and contains 12 exons.

An examination of the association of certain SCARB1 SNPs (including rs4238001 and rs10846744) with quantitative fertility measurements in women undergoing controlled-ovarian stimulation and IVF determined that the non-synonymous SCARB1 SNP, rs4238001, was significantly associated with lower follicular progesterone levels, especially in the Caucasian group. Specifically, the SCARB1 gene is linked to deficiencies of the SR-BI protein, which in turn leads to problems with elevated levels of dysfunctional HDL cholesterol, female infertility, and atherosclerosis. The study found that women carriers of the rs4238001 mutation within the scavenger receptor class B type I (SR-BI) gene (SCARB1) had significantly lower follicular fluid progesterone levels and were unable to become pregnant following in vitro fertilization treatment. Deficiency of SR-BI protein is significantly associated with markedly lower progesterone secretion in human granulosa cells. The effect of SR-BI deficiency on progesterone secretion was independent of lipoproteins in the culture media, and was significantly associated with down-regulation of key steroidogenic genes such as steroidogenic acute regulatory protein (StAR), P450 side-chain cleavage (P450scc) and 3β-hydroxysteroid dehydrogenase (3β-HSD). In addition, women carriers of the rs10846744 SCARB1 variation, and in particular, African American women, had improved responsiveness to in vitro fertilization treatment.

The prevalence of these mutations appears common, demonstrating that this condition is not rare and yet not previously identified in humans with these mutations. Thus, given an initial diagnosis of infertility or reproductive disorder in a female, as a precursor to therapeutic treatment, it would be beneficial to pre-screen for the underlying SCARB1 gene variation and, if positive, to tailor the therapy accordingly.

Genotyping is the process of determining differences in the genetic make-up (genotype) of an individual by examining the individual's DNA sequence and comparing it to a reference sequence. Genotyping can be used for ascertaining the presence of the rs4238001 mutation in a sample taken from a subject. It would be greatly advantageous to conduct a direct mutation analysis by DNA sequencing for the SCARB1 mutation, and to provide a tailored therapeutic regimen to restore fertility by either one or a combination of 1) mediating the flux of cholesterol; and/or 2) amplifying the presence of hormone progesterone. Accordingly, the present invention is a method for pre-screening women experiencing infertility or reproductive disorder by genotyping the SCARB1 mutation rs4238001 and rs10846744 and, if present, providing an efficacious treatment for infertility or reproductive disorder in the SR-BI deficient women.

The cholesterol medication, probucol, lowers the level of cholesterol in the bloodstream by increasing the rate of LDL catabolism. Additionally, probucol may inhibit cholesterol synthesis and delay cholesterol absorption. probucol is a powerful antioxidant which inhibits the oxidation of cholesterol in LDL; this slows the formation of foam cells, which contributes to atherosclerotic plaques. In addition to the drug's anti-oxidant activity it has the ability to inhibit the activity of the ATP cassette transporter, ABCA 1. ABCA 1 is an important transporter that mediates flux of cholesterol and phospholipid to lipid-free apolipoprotein A-I (Apo-AI). By blocking the activity of ABCA 1 with the result of rescuing progesterone synthesis, probucol offers the very real possibility of an efficacious treatment for infertility in SR-BI deficient women.

It is also possible to mimic the hormone progesterone using any of a class of natural or synthetic progestational substances (progestational agents) that mimic some or all of the actions of progesterone. Natural progesterone is obtained primarily from plant sources and is currently available in injectable, intravaginal and oral formulations. An oral micronized progesterone preparation has improved bioavailability and fewer reported side effects compared with synthetic progestins. Some examples of synthetic progestins include norethynodrel (Enovid), norethindrone (many brand names, most notably Ortho-Novum and Ovcon) norgestimate (Ortho Tricyclen, Ortho-Cyclen), norgestrel, levonorgestrel (Alesse, Trivora-28, Plan B, Mirena), medroxyprogesterone (Provera, Depo-Provera), desogestrel, etonogestrel (Implanon), and drospirenone (Yasmin, Yasminelle, YAZ).

The present invention combines the afore-mentioned screening with the selective therapeutic use of the cholesterol medication probucol and/or therapeutic use of the progestational and progestin medications in the treatment of women with SCARB1 deficiency due to gene variations.

SUMMARY OF THE INVENTION

It is, therefore, an object of the present innovation to provide a novel strategy for genotyping to pre-screen for presence of the rs4238001 and rs10846744 mutation in women experiencing infertility or reproductive disorders of unknown, non-physical cause, followed by a tailored therapeutic regimen to restore fertility by either one or a combination of 1) mediating the flux of cholesterol by therapeutic use of the cholesterol medication probucol, and/or 2) amplifying the presence of hormone progesterone by therapeutic use of progestational and progestin medications.

In one embodiment, given an initial diagnosis of infertility, these and other objects are accomplished by a novel combination of pre-screening women to determine by genotyping the presence of the underlying SCARB1 mutation rs4238001 and rs10846744 and, if present, providing an efficacious treatment for the infertility in the SR-BI deficient women by mediating the flux of cholesterol using the cholesterol medication probucol, and/or by amplifying the presence of hormone progesterone by therapeutic use of progestational and progestin medications.

The novelty of the invention is the combination of a companion diagnostic to genetically test humans at risk for three problems: elevated HDL cholesterol, female reproductive problems, and atherosclerosis. The genetic pre-screening is followed by therapeutic strategies that can be used to treat these genetically screened individuals including, but not limited to, cholesterol and triglyceride modifying medications, progestational and estrogen and estrogen-like medications, as well as medications such as probucol and its derivatives to lower HDL cholesterol levels and as antioxidants.

Other objects, features, and advantages of the present invention will become more apparent from the following detailed description of the preferred embodiments and certain modifications thereof.

BRIEF DESCRIPTION OF THE DRAWINGS

Other objects, features, and advantages of the present invention will become more apparent from the following detailed description of the preferred embodiments and certain modifications thereof when taken together with the accompanying drawings in which:

FIG. 1A: *P<0.08 when compared with homozygous major G alleles by ANOVA analysis: FIG. 1B: **P=0.03 compared with homozygous major C alleles.

FIG. 2A: *P=0.04 when compared with homozygous major GG alleles for the rs4238001 SNP by ANOVA analysis. FIG. 2B: *P=0.04 when compared with homozygous major CC alleles for the rs5888 SNP by ANOVA analysis.

DETAILED DESCRIPTION OF THE PREFERRED EMBODIMENT

The present invention is a combination of a genetic test for a variation of the scavenger receptor class B type 1 gene (SCARB1) to ascertain a potential cause of infertility in women combined with the therapeutic use of cholesterol mediating drug and/or progestational or progestin medications in the treatment of said infertility. It will be understood that the present invention is not limited to the particular methods and components, etc., described herein, as these may vary.

As used herein, the singular forms "a," "an," and "the" include the plural reference unless the context clearly dictates otherwise. Thus, for example, a reference to a "protein" is a reference to one or more proteins, and includes equivalents thereof known to those skilled in the art. Any and all references to a SNP by the "rs" designation, for example rs4238001 hereby incorporates the associated nucleotide sequence which is easily retrievable by known methods. Specifically, the nucleotide sequences for rs4238001, rs10846744 are retrievable, for example, from NCBI's dbSNP Entrez database.

Figure 4:
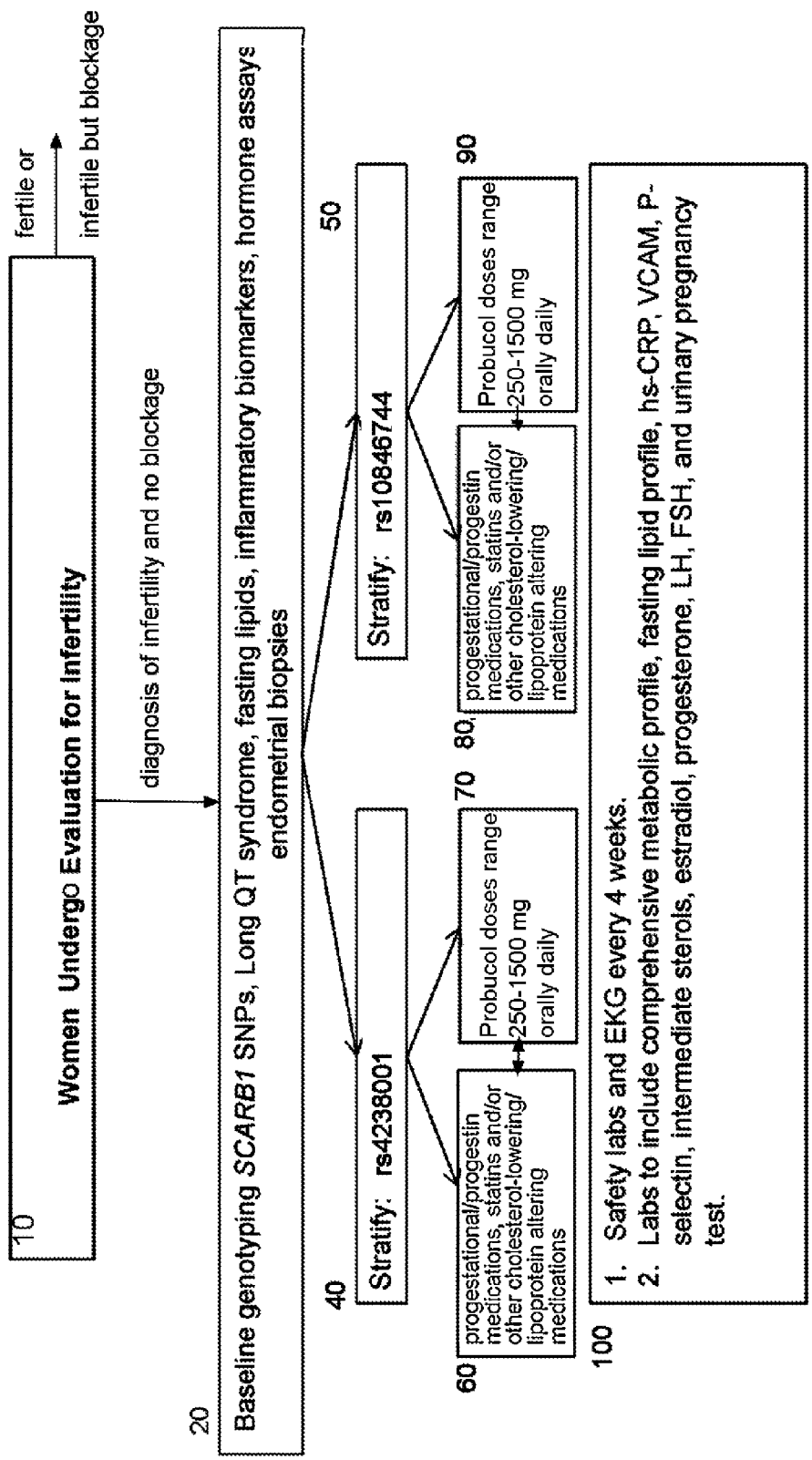
FIG. 4 is a block diagram of an exemplary embodiment of a method for pre-screening and correlation of underlying SCARB1 gene variation to infertility in women and therapeutic use of progestational and other medications in treatment of infertility according to the present invention.

FIG. 4 is a block diagram of an exemplary embodiment of the present method, which begins at step 10 with an initial diagnosis of infertility. This may entail a standard fertility evaluation including a physical examination and review of medical and sexual histories, verification that ovulation is (or is not) occurring, and a hysterosalpingogram (imaging of the fallopian tubes and uterus). Given a diagnosis of infertility and a determination that no physical blockage exists, the method proceeds to step 20.

At step 20, a genetic screening of a biological sample from a subject for the presence of specific allelic variants of one or more polymorphic regions of an SR-BI gene is conducted to determine the presence of the underlying SCARB1 mutation rs4238001 and rs10846744. SR-B1 (SCARB1) is the predominant receptor for HDL cholesterol and plays an important role in reverse cholesterol transport (removal from cells with eventual disposal via the liver). SR-B1 is highly expressed in the liver and steroidogenic tissues such as the ovary. SR-B1 is thought to be critical in maintaining cholesterol stores for steroid production. The presence of both rs4238001 and rs10846744 indicate a risk or susceptibility allele for infertility/reduced fetal viability as detailed below.

Pre-Screening for Polymorphic Changes to the SR-BI Gene

The presence of the rs4238001 and rs10846744 SCARB1 mutation can be determined by a variety of known methods including genotyping. Genotyping for rs4238001 and rs10846744 may be carried out by direct mutation analysis by DNA sequencing of a standard blood test. Genomic DNA is prepared from a whole blood sample purified to isolate DNA from the blood sample. The purity and quantity of DNA may be checked by spectrophotometry. The DNA is added to a plate and genotyped with an oligo-ligation assay (for example, SNPlex® is a suitable platform for SNP genotyping sold by Applied Biosystems of Foster City, Calif., USA) following manufacturer guidelines. The oligo-ligation assay uses fluorescent dye-labeled probes to indicate presence of one or both rs4238001 and rs10846744 mutations.

Other methods useful in screening for the presence of a specific allelic variant of one more polymorphic regions of an SR-BI gene include, for example, DNA sequencing, hybridization techniques, PCR based assays, fluorescent dye and quenching agent-based PCR assay (Taqman PCR detection system), RFLP-based techniques, single strand conformational polymorphism (SSCP), denaturing gradient gel electrophoresis (DGGE), temperature gradient gel electrophoresis (TGGE), chemical mismatch cleavage (CMC), heteroduplex analysis based system, techniques based on mass spectroscopy, invasive cleavage assay, polymorphism ratio sequencing (PRS), microarrays, a rolling circle extension assay, HPLC-based techniques, DHPLC-based techniques, oligonucleotide extension assays (OLA), extension based assays (ARMS, (Amplification Refractory Mutation System). ALEX (Amplification Refractory Mutation Linear Extension), SBCE (Single base chain extension), a molecular beacon assay, invader (Third wave technologies), a ligase chain reaction assay, nuclease assay-based techniques, hybridization capillary array electrophoresis (CAE), pyrosequencing, protein truncation assay (PTT), immunoassays, haplotype analysis, and solid phase hybridization (dot blot, reverse dot blot, chips), etc.

One type of screening method is allele specific hybridization using probes overlapping the polymorphic site and having about 5, 10, 20, 25, or 30 nucleotides around the polymorphic region. In one embodiment of the invention, several probes capable of hybridizing specifically to allelic variants are attached to a solid phase support, e.g., a "chip". Oligonucleotides can be bound to a solid support by a variety of processes, including lithography. Indeed, a chip can hold up to 250,000 oligonucleotides (GeneChip®, Affymetrix®).

In one embodiment, a chip comprises all the allelic variants of at least one polymorphic region of an SR-BI gene. The solid phase support is then contacted with a test nucleic acid and hybridization to the specific probes is detected. Accordingly, the identity of numerous allelic variants of one or more genes can be identified in a simple hybridization experiment.

In some screening methods it is necessary to first amplify at least a portion of an SR-BI gene prior to identifying the allelic variant. Amplification can be performed, e.g., by PCR, according to methods known in the art. In one embodiment genomic DNA of a cell is exposed to two PCR primers and amplification for a number of cycles sufficient to produce the required amount of amplified DNA.

In addition to the methods recited or incorporated by reference above, the present invention further provides methods for detecting single nucleotide polymorphisms (SNPs) in an SR-BI gene. Because SNPs constitute sites of variation flanked by regions of invariant sequence, their analysis requires no more than the determination of the identity of the single nucleotide present at the site of variation and it is unnecessary to determine a complete gene sequence for each patient Several methods have been developed to facilitate the analysis of such single nucleotide polymorphisms.

The methods described herein may be performed, for example, by utilizing pre-packaged diagnostic kits, such as those described above, comprising at least one probe or primer nucleic acid described herein, which may be conveniently used, e.g., to determine whether a subject has or is at increased risk of developing a disease associated with a specific SR-BI allelic variant.

The methods of the present invention, including methods for identifying the presence of an allelic variant or SNP in the SR-BI gene of a subject may be combined with other information or parameters using the methods well known in the art to aid in the identification of subject with deficiency in the SR-BI protein. Such additional information or parameters may include, but is not limited to, lipid levels, hormone levels, adipokines, nitric oxide metabolites, serum inflammatory markers, and/or cross-correlation with diagnoses of subclinical atherosclerosis or coronary heart disease (CHD). The significant association of SCARB1 variant, rs10846744, with coronary heart disease (CHD) was shown in Manichaikul et al. (Arterioscler Thromb Vase Biol 2012; 32:1991-1999). There is now evidence that the SCARB1 variant, rs4238001, is also significantly associated with CHD. The present inventor has shown by meta-analysis that rs4238001 is associated with a 50% increased risk for CHD.

Without further elaboration, it is believed that one skilled in the art, using the preceding description, can utilize the present invention to the fullest extent. Given the foregoing evidence that the SCARB1 variant, rs4238001, is also significantly associated with CHD, statins and other cholesterol/lipoprotein altering medications can be used alone or in combination with probucol as a therapeutic strategy for treatment of either lipid, CHD, or reproductive disorders associated with SCARB1 variants rs10846744 and rs4238001.

Referring back to FIG. 4 and given the presence of one or both rs4238001 and rs10846744 mutations, at steps 40, 50, the sequencing results as described, above are used to stratify patients on the basis of their underlying SCARS mutations, and particularly the rs4238001 and rs10846744 mutations. The present method initiates therapeutically-effective regimens of the cholesterol medication probucol at steps 70, 90, and/or therapeutically-effective regimens of progestational/progestin medications at steps 60, 80. An exemplary regimen of probucol treatment may comprises three-to-four months of low-dose treatment (250 mg/day), and even more preferably comprises one-to-two months of said treatments. At step 100 monitoring comprises monthly safety labs with comprehensive profiles and EKGs to determine effect on oxidation and on plasma-HDL cholesterol. An exemplary regimen of progestational/progestin treatment similarly comprises three-to-four months of treatment, and at step 100 monitoring comprises monthly safety labs with comprehensive profiles and EKGs to determine effect on LDL oxidation and on plasma-HDL cholesterol.

The progestational drug may be natural micronized progesterone or any synthetic progestin, such as medroxyprogesterone (e.g., Provera™ taken in 2.5 mg, 5 mg or 10 mg tablets once daily over the same three-to-four months). Alternatively, any of the eight known progestins may be used including Norethindrone (a first-generation progestin of low progestational and slight estrogenic activity), Norethindrone Acetate (a progestin of low progestational activity and slight estrogenic affects), Ethynodiol diacetate (a first-generation progestin of medium progestational activity), Levonorgestrel (a second-generation progestin with high progestational and androgenic effects), Norgestrel (a second-generation progestin with high progestational and strong antiestrogen effects), Desogestrel (a third-generation progestin with high progestational selectivity, minimizing androgenic effects), Norgestimate (a third-generation progestin with high progestational activity and slight estrogenic effects), and Drospirenone (third generation with high progestational activity and low androgenic activity). Each of the foregoing have various contra-indications and the selection is necessarily patient specific.

By inhibiting the oxidation of cholesterol in LDLs and inhibiting the activity of the ATP cassette transporter, ABCA 1, probucol has the result of rescuing progesterone synthesis, thereby providing an efficacious treatment for infertility in SR-BI deficient women. Similarly, by directly supplementing progesterone synthesis using a regimen of progestational/progestin treatment, an equally efficacious treatment for infertility in SR-BI deficient women is provided. The present method combines genetic pre-screening with the selective therapeutic use of the cholesterol medication probucol and/or therapeutic use of the progestational and progestin medications in the treatment of women with SCARB1 deficiency due to gene variations.

One skilled in the art will readily understand that other suitable therapeutic strategies may be employed to treat these genetically screened individuals including, but not limited to, any other cholesterol and triglyceride modifying medications, progestational and estrogen and estrogen-like medications, as well as medications similar to probucol for lowering HDL cholesterol levels and as antioxidants.

EXAMPLES

Materials and Methods:

The association of certain key SCARB1 SNPs with fertility measurements such as progesterone levels and measurements of embryo/fetal viability were determined in women undergoing IVF to investigate the role of SCARB1 in human female reproductive physiology. The rationale for studying women undergoing IVF was due to the availability of granulosa cells and follicular fluid as by-products of oocyte retrievals.

Granulosa cells were isolated from 320 women undergoing controlled-ovarian hyperstimulation (COH) and IVF, which provided a final study pool of 274 women and biological samples for genetic testing.

Materials:

Chemical reagents and solvents were obtained from Sigma-Aldrich (St Louis, Mo., USA), the MiniKit™ QIAmp-DNA™ was from Qiagen (Valencia, Calif., USA) and the progesterone ELISA™ kit was from ALPCO (Salem, N.H., USA).

Granulosa Cell Retrieval and Isolation:

Follicular aspirates from each subject were centrifuged at 1500 g for 10 min at 4° C. Follicular fluid was then collected and an aliquot was extracted for progesterone measurement. The cell pellet was re-suspended in phosphate-buffered saline (PBS), overlaid onto 40% (v/v) Percoll® solution from Sigma-Aldrich and centrifuged at 2500 g at 4° C. Granulosa cells at the Percoll®-PBS interface were aspirated, re-suspended in PBS and pelleted by centrifugation at 1500 g. This step was repeated two times and the recovered cells were processed for genomic DNA extraction.

Clinical Fertility Measurements:

Subjects underwent COH and oocyte aspiration. Embryo transfers were performed on Day 3 or 5 after retrieval. I.M. progesterone (50 mg daily) or vaginal progesterone (100 mg three times daily) were initiated the day following oocyte retrieval for luteal phase support. A serum pregnancy test was performed 14 days after embryo transfer by measuring serum hCG. Clinical pregnancy was defined as the presence of a gestational sac(s) and the data were coded as categorical '0=no' for no gestational sac(s) and '1=yes' for the presence of gestational sac(s). Patients were followed by transvaginal ultrasound until the detection of fetal heart motion (Day 42 post-embryo transfer) and the data were coded as categorical '0=no' for heartbeat(s) and '1=yes' for heartbeat(s).

Follicular Fluid Analyses:

Progesterone levels were measured in follicular fluid extracts. The rationale for measurement of progesterone in follicular fluid was based on its availability and the direct contribution of ovarian progesterone secretion in the follicular fluid. Each 100 μl sample of follicular fluid was placed into a glass tube and 1 ml of petroleum ether was added. The tube was subjected to vortexing for 30 sec at maximum speed to separate the organic and inorganic phases. The organic phase was transferred into a new glass tube and the solvent was evaporated under a stream of N2. The residue was dissolved in phosphate buffered saline (PBS) and analyzed by ELISA using a commercially available kit. The intra- and inter-assay coefficient of variation for the assay is 7.3 and 11.3%, respectively.

DNA Sequencing:

Genomic DNA was extracted from granulosa cells using a QIAamp® DNA Mini Kit. The following SCARB1 SNPs (gene location) were characterized by direct sequencing in both directions of PCR products: rs4238001 (exon 1), rs10846744 (intron 1), rs5891 (exon 3), rs2278986 (intron 3) and rs5888 (exon 8). Sequence comparisons were determined using the Sequencher Program v.4.0 (Gene Code). The primer sequences and PCR conditions are available from the authors upon request. The rationale for selecting these particular SNPs was based on previously reported significant associations of these SNPs with phenotypic traits.

Statistical Analysis:

The differences in SCARB1 genotype frequencies across the racial/ethnic groups and the association of SCARB1 SNPs with clinical fertility measurements were measured by $\chi 2$ analysis.

Results are shown below in Table 1.

TABLE 1

Gene location and genotype frequencies of SCARB1 SNPs

| Identification | Location | Amino acid change | Caucasian | | | Hispanic | | | African American | | | Asian-American | | | P-value across all groups |
|---|---|---|---|---|---|---|---|---|---|---|---|---|---|---|---|
| | | | GG | GA | AA | GG | GA | AA | GG | GA | AA | GG | GA | AA | |
| rs4238001, G → A | Exon 1 | Yes | (97) | (3) | (0) | (100) | (0) | (0) | (93) | (7) | (0) | (97) | (3) | (0) | n.s. |
| | | | CC | CG | GG | CC | CG | GG | CC | CG | GG | CC | CG | GG | |
| rs10847644, C → G | Intron 1 | No | (89) | (4) | (7) | (85) | (15) | (0) | (45) | (13) | (42) | (53) | (21) | (26) | <0.0001 |

TABLE 1-continued

Gene location and genotype frequencies of SCARB1 SNPs

| Identification | Location | Amino acid change | Caucasian | | | Hispanic | | | African American | | | Asian-American | | | P-value across all groups |
|---|---|---|---|---|---|---|---|---|---|---|---|---|---|---|---|
| rs5891, G → A | Exon 3 | Yes | GG (98) | GA (1) | AA (1) | GG (100) | GA (0) | AA (0) | GG (99) | GA (1) | AA (0) | GG (100) | GA (0) | AA (0) | n.s. |
| rs2278986, T → C | Intron 3 | No | TT (39) | TC (50) | CC (11) | TT (43) | TC (36) | CC (21) | TT (61) | TC (33) | CC (6) | TT (53) | TC (29) | CC (18) | 0.03 |
| rs5888, C → T | Exon 8 | No | CC (39) | CT (51) | TT (17) | CC (29) | CT (50) | TT (21) | CC (54) | CT (37) | TT (10) | CC (38) | CT (50) | TT (12) | n.s |

The association of SCARB1 SNPs with follicular progesterone levels was performed using one-way analysis of variance (ANOVA). Each SCARB1 SNP was added to the multivariate stepwise regression analyses individually and together to assess whether the SNPs were independent predictors of follicular progesterone levels. Threshold significance values for selection and retention in the stepwise analysis were 0.25 and 0.10, respectively. All analyses were performed using JMP Genomics 4.2 (SAS Institute, Cary, N.C., USA). Probability values <0.05 were considered statistically significant.

Results:

With reference to Table 1, the study population consisted of 274 adult women with a mean age of 36.4±4.6 years (range 23-46 years). The self-described racial/ethnic composition of the group consisted of 55% Caucasian (n=152), 25% African-American (n=68), 12% Asian (n=34), 5% Hispanic, (n=14) and 2% other (n=6). Other general characteristics of the entire group included a mean BMI of 26.8±7.1 (range 16.8-53.3), and previous IVF attempts of 1.8±1.5.

The gene location and genotype frequencies of the SCARB1 SNPs in this population are shown in Table 1. Significant differences between genotype frequencies of the rs10847644 (P<0.0001) and rs2278986 (P=0.03) were observed across all the racial/ethnic groups. However, there were no observed differences in the SCARB1 genotype frequencies between the Caucasian and Hispanic groups, nor between the African-American and Asian groups. There were significant differences in the rs10846744 (P<0.0001), rs2278986 (P=0.01) and rs5888 (P=0.01) genotypes between the Caucasian and African-American groups. The genotype frequency of rs10847644 was also significantly different between Caucasians and Asians (P<0.0001).

Figure 1:
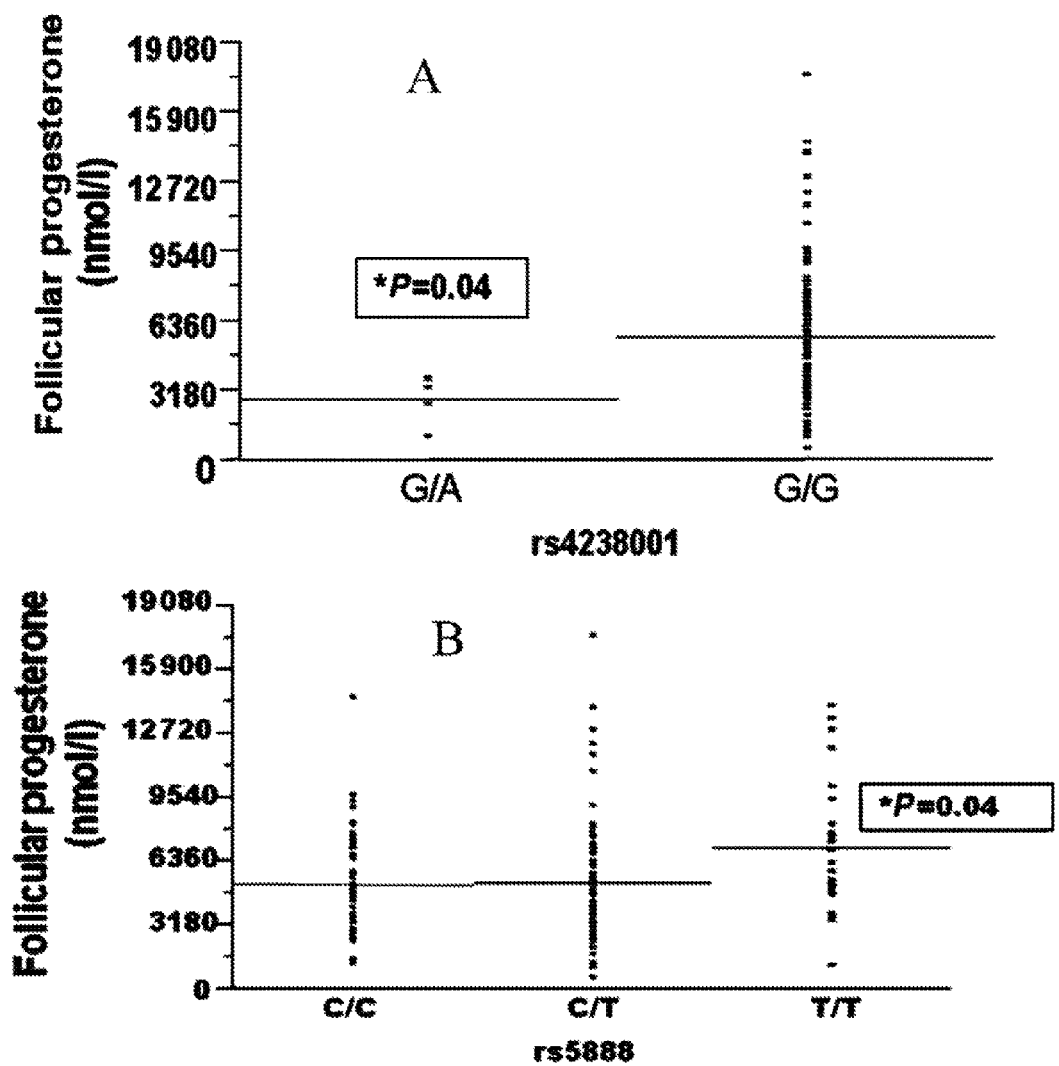
FIGS. 1A and 1B depict the association of SCARB1 SNPs with follicular progesterone levels in the entire cohort of infertile women undergoing IVF. SCARB1 SNPs were genotyped by direct sequencing and follicular progesterone levels were measured in lipid extracts of follicular fluid using a commercially available assay.
Figure 2:
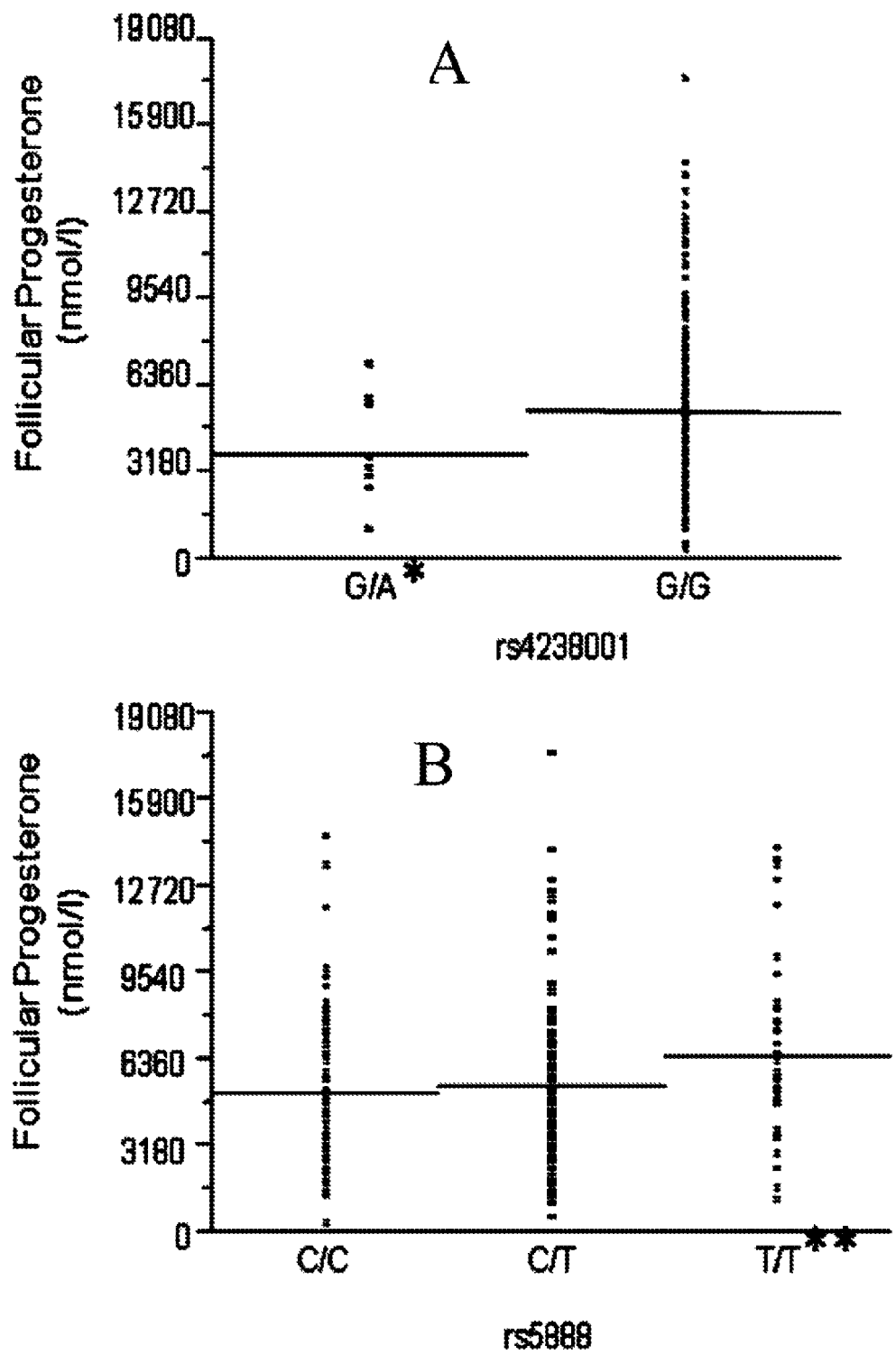
FIG. 2 depicts the association of SCARB1 SNPs with follicular progesterone levels in the Caucasian group.

The univariate association of the SCARB1 SNPs with follicular progesterone levels was then studied. As shown in FIG. 1A, for the entire group, carriers of the minor A allele for the rs4238001 SNP had lower follicular progesterone levels compared with homozygous carriers of the major G allele (29% lower, P<0.08). In contrast, subjects who were homozygous for the minor T allele of the rs5888 SNP had significantly higher follicular progesterone levels compared with subjects homozygous for the major C allele (homozygous major CC: 5061±285 nmol/l: heterozygous CT: 5367±260; homozygous minor TT: 6498±462) (P=0.03) (FIG. 1B). In the Caucasian group, carriers of the minor allele for rs4238001 had lower follicular progesterone levels (2528±1517) when compared with homozygous carriers of the major allele (5629±254, 55% lower, P=0.04) (FIG. 2A). In the Caucasian group, homozygous carriers of the minor allele for rs5888 had higher follicular progesterone levels (homozygous major CC: 5148±450 nmol/l: heterozygous CT: 5346±359; homozygous minor TT: 7041±623) (P=0.04) (FIG. 2B). In the African-American group, there were no significant univariate associations of SCARB1 SNPs with follicular progesterone levels.

Multivariate regression analysis was also performed in the Caucasian group using age, BMI, baseline FSH levels, and baseline LH levels, then in a stepwise fashion separately included each of the five SCARB1 SNPs as independent covariates in the initial model, with follicular progesterone as the dependent variable. Following stepwise regression, only the rs4238001 SNP remained as an independent predictor of follicular progesterone levels (P=0.03). None of the other variables, including BMI, were independent predictors of follicular progesterone levels.

Figure 3:
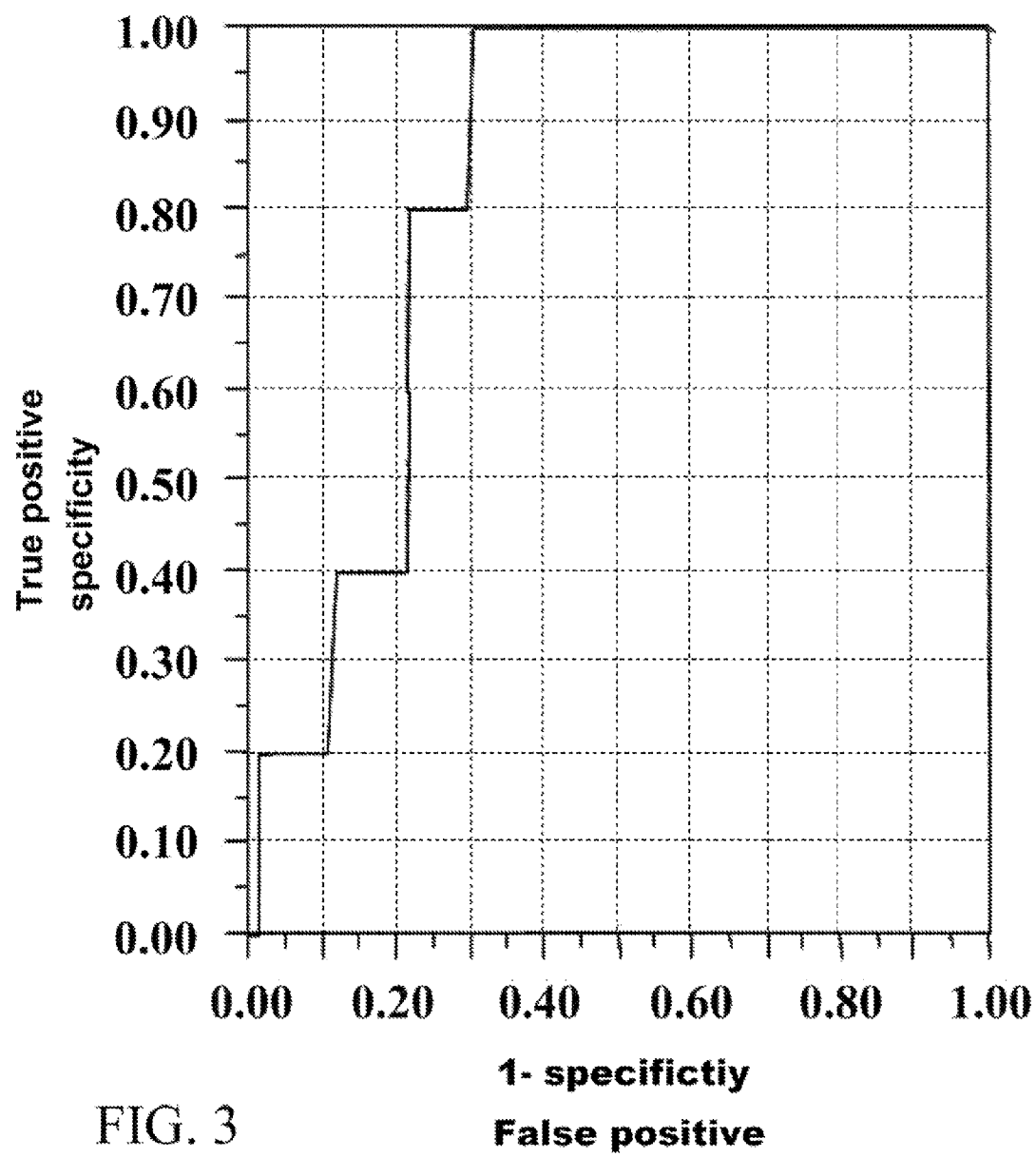
FIG. 3 is the ROC curve for prediction of rs4238001 based on follicular progesterone levels in the Caucasian group. Sensitivity 0.80, false-positive rate 0.22, P=0.03.

Given that the rs4238001 remained as an independent predictor for follicular progesterone levels in the Caucasian group, the sensitivity and specificity of follicular progesterone as a predictor of the rs4238001 SNP was examined using the receiver operating characteristic (ROC) analysis. As shown in FIG. 3, follicular progesterone was highly predictive with a sensitivity of 0.80 and a false-positive rate of 0.22 (P=0.03), with a cutoff value of <3682 nmol/l (1158 ng/ml).

The association of each SNP with clinical fertility measurements was next examined, such as the number of retrieved and fertilized oocytes, the number of embryos transferred, clinical pregnancy and fetal heartbeat(s). For the entire pool we found a significant association between rs4238001 and heartbeat(s), with carriers of the minor A allele (n=9) not having any viable fetuses at Day 42 post-embryo transfer (zero heartbeats) when compared with carriers homozygous for the major G allele (n=63 with heartbeats, P=0.04, $\chi 2$).

A significant association was also observed between rs10846744 and the number of retrieved oocytes (homozygous major CC: 9.3±0.5; heterozygous CG: 10.4±1.7: homozygous minor GG: 12.3±1.1, P=0.05). For clinical pregnancy there was a significant association across the genotypes (P=0.04, $\chi 2$): homozygous major CC (n=158): 28% with gestational sacs; heterozygous CG carriers (n=15): 60% with gestational sacs; and homozygous minor GG carriers (n=38): 32% with gestational sacs. For fetal heartbeats (categorical classification), there was a significant association across the genotypes (P=0.03, $\chi 2$): homozygous major CC: 27% with heartbeats; heterozygous CG carriers: 60% with heartbeats; and homozygous minor GG carriers: 29% with heartbeats.

In the Caucasian group, There was not a significant association between any of the SCARB1 SNPs and the clinical fertility parameters. However, in the African-American group, there was a significant association between rs10846744 and clinical pregnancy (P=0.006, $\chi 2$): homozygous major CC (n=23): 35% with gestational sacs; heterozygous CG carriers (n=7): 86% with gestational sacs; and homozygous minor GG carriers (n=21): 19% with gestational sacs. For fetal heartbeats (P=0.005, $\chi 2$): homozygous major CC: 30% with heartbeats; heterozygous CG carriers: 86% with heartbeats; and homozygous minor GG carriers: 19% with heartbeats.

Study results showing significantly lower follicular progesterone levels in women carriers of the minor A allele for rs4238001, especially in the Caucasian group (FIG. 2), are consistent with those recently reported by others in the SR-BI KO female mice which determined that serum progesterone levels were 50% lower in the female SR-BI KO mice when compared with wild-type mice. A mechanism by which SR-BI protein deficiency would impair progesterone secretion in cultured human granulosa cells was recently identified and a novel, lipoprotein independent role of SR-BI deficiency in impairing de novo cholesterol synthesis, which led to down-regulation of key steroidogenic enzymes such as P450scc and 3β-HSD was reported.

In the univariate association analyses, it was found that the rs5888 SNP was significantly associated with higher follicular progesterone levels in the entire group, and this was driven primarily by the association found in the Caucasian group (FIGS. 2A and B). However, in the multivariate regression analyses, only the rs4238001 SNP remained as an independent predictor of follicular progesterone levels. It was found that the rs4238001 SNP was significantly associated with lower follicular progesterone levels, and follicular progesterone levels were in turn highly sensitive and specific in predicting the presence of the SNP (the ROC analysis, FIG. 3). This polymorphism is a non-synonymous SNP that causes an amino acid change (glycine→serine) at Position 2 in the SR-BI protein.

Looking at subjects with hyperalphalipoproteinemia (HALP, defined as having HDL cholesterol >60 mg/dl), the minor allele frequency (MAF) of this SNP in our HALP population was 12%. In other populations as reported in the Single Nucleotide Polymorphism database (dbSNP) the frequency varies between 2 and 13%. Using an in vitro approach, it was demonstrated that the rs4238001 SNP significantly increased SR-BI protein degradation; thus, this SNP is causal in inducing lower SR-BI protein expression. Consequently, results in this current study are consistent with in vitro results. Follicular progesterone levels [values <3682 nmol/l (1158 ng/ml)] are highly predictive of SR-BI protein deficiency, strongly suggestive of the clinical utility of screening infertile women for SR-BI deficiency by genotyping for this particular SCARB1 SNP. The association of rs4238001 with heartbeats was particularly compelling as carriers of the minor A allele had no viable fetuses at Day 42 following embryo transfer; this despite routine pharmacological progesterone supplementation to all subjects following embryo transfer. This suggests that simple replacement of progesterone does not overcome problems with clinical fertility outcomes in infertile women carriers of the SCARB1 rs4238001 and rs10846766 SNPs.

In conclusion, it has here been shown that SR-BI exerts an independent effect on follicular progesterone levels, and follicular progesterone levels can be highly sensitive and specific predictors of rs4238001. This SNP and rs10846744 were also significantly associated with poor fetal viability, which may indicate a significant underlying mechanism for SR-B1 in human reproduction which is highlighted even in the setting of COH, IVF and exogenous hormone supplementation. This establishes the utility of this novel strategy for genotyping to pre-screen for presence of the rs4238001 and rs10846744 mutation in women experiencing infertility or reproductive disorders of unknown, non-physical cause.

As stated above, the genetic pre-screening is followed by a tailored therapeutic regimen to restore fertility by either one or a combination of 1) mediating the flux of cholesterol by therapeutic use of the cholesterol medication probucol, and/or 2) amplifying the presence of hormone progesterone by therapeutic use of progestational and progestin medications.

The same genetic pre-screening may be used as an indicator of atherosclerosis/CHD, followed by administering a statin or other cholesterol/lipoprotein altering medication alone or in combination with probucol as a therapeutic for atherosclerosis risk in human carriers of the SCARB1 variants, rs10846744 and rs4238001.

Having now fully set forth the preferred embodiment, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

I claim:

1. A method for treating infertility in a human adult female subject comprising the steps of:
   a) confirming that the human adult female subject has been medically diagnosed with infertility,
   b) performing a medical examination to eliminate physical obstruction as a cause of said diagnosed infertility in said human adult female subject,
   c) obtaining a whole blood sample from said human adult female subject,
   d) purifying said whole blood sample,
   e) isolating nucleic acid from said purified blood sample,
   f) conducting a genetic gest on said isolated nucleic acid, comprising a microarray assay or a fluorescent allele specific polymerase chain reaction (PCR) based assay that detects the allele for the rs4238001 polymorphism in the SCARB1 gene in said human adult female subject,
   g) detecting the A allele for rs4238001 in said isolated nucleic acid from said human adult female subject,
   h) administering a pharmacologically effective regimen of probucol to said human adult female subject to mediate cholesterol in said human adult female subject's bloodstream.

2. The method of claim 1 further comprising periodically administering a comprehensive metabolic profile to correct for one or more of a cholesterol, progesterone, or estrogen hormone imbalance.

3. The method of claim 1 wherein said genetic test comprises amplification of said isolated nucleic acid.

4. The method of claim 1 wherein said genetic test further comprises allele specific oligonucleotide probes.

5. The method of claim 1 wherein said genetic test further comprises direct sequencing.

6. The method of claim 1 comprising administering a pharmacologically effective regimen of probucol in periodic doses over a period within a range of from 3 to 9 months and monitoring cholesterol in said human adult female subject's bloodstream during the administration period.

7. A method for treating infertility in a human adult female subject comprising the steps of:
   a) selecting a human adult female subject who has been medically diagnosed with infertility,
   b) obtaining a whole blood sample from said human adult female subject,
   c) purifying said whole blood sample,
   c) isolating nucleic acid from said purified blood sample,
   c) conducting a genetic gest on said isolated nucleic acid, comprising a microarray assay or a fluorescent allele specific polymerase chain reaction (PCR) based assay that detects the allele for the rs4238001 polymorphism in the SCARB1 gene in said human adult female subject, f) detecting the A allele for rs4238001 in said isolated nucleic acid from said human adult female subject, g) administering a pharmacologically effective regimen of probucol to said human adult female subject to mediate cholesterol in said human adult female subject's bloodstream.

8. The method of claim 7, further comprising increasing progesterone in said human adult female subject.

9. The method of claim 7, further comprising a sub step in the genetic test of step e, selected from the group consisting of administering an allele specific oligonucleotide probe or direct sequencing.

10. The method of claim 7 comprising administering a pharmacologically effective regimen of probucol in periodic doses over a period within a range of from 3 to 9 months and monitoring cholesterol in said human adult female subject's bloodstream during the administration period.

* * * * *